United States Patent
Scherl et al.

(10) Patent No.: US 6,235,268 B1
(45) Date of Patent: May 22, 2001

(54) ANTIPLAQUE ORAL COMPOSITION AND METHOD

(75) Inventors: Dale S. Scherl, Somerset; Lori Szeles, Old Bridge, both of NJ (US); Tao Xu, Newton, MA (US); Abdul Gaffar, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/514,605

(22) Filed: Feb. 28, 2000

(51) Int. Cl.$^7$ ................... A61K 7/16; A61K 7/18
(52) U.S. Cl. .................. 424/49; 424/52
(58) Field of Search ............... 424/49–58

(56) References Cited

U.S. PATENT DOCUMENTS

| | | | | |
|---|---|---|---|---|
| 3,993,779 | * | 11/1976 | Dunnenberger et al. | 424/331 |
| 4,117,107 | * | 9/1978 | Shapiro, I et al. | 424/54 |
| 4,117,108 | * | 9/1978 | Shapiro, II et al. | 424/54 |
| 4,490,353 | * | 12/1984 | Crawford et al. | 424/52 |
| 4,528,132 | * | 7/1985 | Curtis et al. | 424/54 |
| 4,632,825 | * | 12/1986 | Ferlauto, I et al. | 424/52 |
| 4,774,077 | * | 9/1988 | Ferlauto, II et al. | 424/52 |
| 4,839,158 | * | 6/1989 | Michaels, I | 424/54 |
| 5,275,804 | * | 1/1994 | Michaels, II | 424/54 |
| 5,403,579 | * | 4/1995 | Michaels, III | 424/54 |
| 5,681,548 | * | 10/1997 | Esposito et al. | 424/49 |

FOREIGN PATENT DOCUMENTS

| | | | |
|---|---|---|---|
| 03170414 A2 | * | 7/1991 | (JP) . |
| 04134025 A2 | * | 5/1992 | (JP) . |
| 11049654 A2 | * | 2/1999 | (JP) . |

* cited by examiner

Primary Examiner—Shep K. Rose
(74) Attorney, Agent, or Firm—Paul Shapiro

(57) ABSTRACT

An oral antiplaque composition comprising an orally acceptable vehicle and an effective antiplaque amount of 4-alkoxy substituted 2-hydroxy benzophenone compound having the following formula:

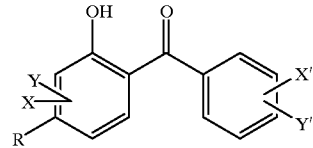

where X, Y, X' and Y' represent hydrogen, and lower straight chain or branched $C_1$–$C_4$ alkyl radicals, $C_3$–$C_6$ cycloalkyls and R represents lower $C_1$–$C_8$ alkoxy radicals.

14 Claims, No Drawings

ANTIPLAQUE ORAL COMPOSITION AND METHOD

BACKGROUND OF THE INVENTION

1. Field of the Invention

This invention relates to an antiplaque oral composition containing an alkoxy substituted 2-hydroxy benzophenone which exhibits heightened antibacterial efficacy against plaque causing oral bacteria.

2. The Prior Art

Dental plaque is a soft deposit which forms on teeth as opposed to calculus which is a hard calcified deposit on teeth. Unlike calculus, plaque may form on any part of the tooth surface, particularly at the gingival margin. Hence, beside being unsightly, it is implicated in the occurrence of gingivitis.

It is difficult to predict the efficacy of antibacterial agents when incorporated in oral compositions. For example, cationic antibacterial materials such as chlorhexidine, benzthonium chloride and cetyl pyridinium chloride have been used by the art as antibacterial antiplaque agents in oral compositions. However, such agents are generally not effective when there is also present anionic surfactants required for the effective performance of oral compositions such as toothpaste and mouthrinses. Nonionic antibacterial materials are compatible with anionic ingredients in oral compositions and nonionic halogenated hydroxydiphenyl ethers such as Triclosan have been effectively employed in oral compositions as antibacterial antiplaque agents when admixed with neutral materials such as humectants, abrasives and thickeners used in the formulation of oral compositions. Notwithstanding the antibacterial efficacy of Triclosan, there is a continuing interest in the oral composition field for antibacterial agents which are compatible with anionic surfactants present in such compositions.

It is known to the art, U.S. Pat. No. 3,993,779, that 2-hydroxy benzophenone, and certain alkyl, benzene, halogen and cyclohexyl-substituted 2-hydroxy benzophenones have antibacterial action and are suitable for use as preservatives and disinfectants.

Japanese Patent 03170414 discloses the use of 2-hydroxybenzophenone in toothpaste, for the prevention and treatment of periodontal disorders. Although effective for this purpose, the antiplaque efficacy of the toothpaste containing the hydroxybenzophenone compound is limited and an improvement in its efficacy is required for acceptability in commercial use.

SUMMARY OF THE INVENTION

In accordance with the present invention there is provided an oral antiplaque composition exhibiting heightened antibacterial efficacy against plaque causing oral bacteria which is comprised of an alkoxy substituted 2-hydroxybenzophonone orally acceptable vehicle containing a mixture of an anionic surfactant such as sodium lauryl sulfate and a betaine based surfactant the 4-alkoxysubstituted 2-hydroxy benxophenone having the following formula:

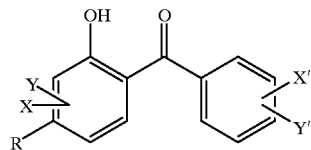

where X, Y, X' and Y' represent hydrogen, and lower straight chain or branched alkyl radicals such as $C_1$–$C_4$ radicals such as methyl, ethyl, propyl, isopropyl and butyl, or cycloalkyls such as $C_3$–$C_6$, such as cyclopropyl, cyclobutyl or cyclohexyl, and R represents lower alkoxy radicals, such as $C_1$–$C_8$ radicals, such as methoxy, ethoxy, propoxy, and octyloxy radicals or combinations thereof and the salts thereof.

As will hereinafter be disclosed, the presence in the oral composition vehicle of the mixture of anionic surfactant and betaine compound provides an unexpected increase the antiplaque efficacy of the oral composition.

DETAILED DESCRIPTION OF THE PREFERRED EMBODIMENTS

Representative 4-alkoxy substituted 2-hydroxyphenone compounds useful in the practice of the present invention include but are not limited to 2-hydroxy-4-ethoxybenzophenone, 2-hydroxy-4-isopropoxybenzophenone, 2-hydroxy-4-methoxy-4'-t-butyl-benzophenone, 2-hydroxy-4-methoxy-5-methyl-benzophenone. The compound 2-hydroxy-4-methoxybenzophenone is preferred for use in the present invention as the very low toxicity indicated by an LD-50 (oral/rats) of 12.8 g/kg, LD-50 being a standard measure of acute toxicity and defined as lethal dose at which 50% of the rat population dies, Merck Index, Eleventh Ed., Merck & Co., Inc., Rahway, N.J., USA (1989). The fact that the 4-alkoxy substituted 2-hydroxyphenone is non-halogenated suggests that it will be suitable as an ingredient in daily user oral hygiene products such as dentifrice and mouth rinse formulations and will be easily biodegradable.

The 4-alkoxy 2-hydroxy benzophenone is incorporated in the oral compositions of the present invention in a non-toxic, effective antiplaque amount, typically in a range of about 0.003 to about 5%, preferably about 0.005 to about 3% and more preferably about 0.02 to about 1% by weight.

The surfactant mixture present in the compositions of the present invention in addition to their normal functionality to achieve thorough and complete dispersion of the 4-alkoxy substituted 2-hydroxybenzophenone antibacterial agent throughout the oral cavity also unexpectedly increase the antibacterial efficacy of the hydroxybenxophenone compound. The anionic surfactant and betaine based surfactants are present in the composition at a weight ratio of about 0.5:2.0 and preferably about 1:1.

Examples of anionic surfactants useful in the practice of the present invention include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2- dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

The term "betaine based surfactant" includes amphoteric compounds such as amidobetaine compounds such as cocoamidoethylbetaine, cocoamidopropyl betaine, laurylamido propyl betaine and related compounds as for example fatty acid amido alkyl betaines and mixtures thereof.

The anionic surfactant is incorporated in the oral composition, a concentration of about 0.5 to about 2% by weight and preferably 0.75 to 1% by weight and the betaine based surfactant is incorporated in the oral composition at a concentration of about 0.5 to about 2% by weight and preferably about 0.5 to about 1% by weight.

Linear molecularly dehydrated polyphosphate salts can be optionally employed herein as anticalculus agents. They are well known, being generally employed in the form of their wholly or partially neutralized water soluble alkali metal (e.g. potassium or sodium) or ammonium salts, and any mixtures thereof. Representative examples include sodium tripolyphosphate, monosodium triacid,-, disodium diacid-, trisodium monoacid-, and tetrasodium-pyrophosphates, the corresponding potassium salts and the like. In the present invention, they can be employed in the oral compositions in approximate weight amounts of about 0.1 to about 3%, typically about 1 to about 2.5%, more typically about 1.5 to about 2%, especially about 2%. Preferred anticalculus agents are tetraalkali metal pyrophosphates such as tetrasodium and tetrapotassium pyrophosphates, and mixtures thereof.

Fluoride ions may also be included in the oral compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

The oral composition of the present invention may be a solution of ingredients such as a mouthrinse or it maybe a semi-solid such as a toothpaste or gel dentifrice.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15 to about 40% by weight and glycerine, sorbitol and/or the alkylene glycol (preferably propylene glycol) typically total about 20–75% by weight of the oral composition, more typically about 25 to about 60% by weight.

When the oral composition is substantially semi-solid or pasty in character, such as a toothpaste or gel, the dentifrice vehicle may contain a dentally acceptable abrasive material such as sodium bicarbonate or water insoluble abrasive material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, and mixtures thereof.

The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

In the aspect of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerine, sorbitol or an alkylene glycol such as polyethylene glycol or preferably propylene glycol may be present in amount of about 10–30% by weight. Mouthrinses typically contain about 50–85% of water, about 0 to 20% by weight of a non-toxic alcohol and about 10–40% by weight of the humectant.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Agents used to diminish tooth sensitivity such as potassium chloride, potassium nitrate and potassium citrate can also be included in the oral compositions of the present invention at concentrations of about 0.1 about 10% by weight.

Polycarboxylate polymers may be included in the oral composition and those prepared for use in the practice of the present invention include a natural or synthetic anionic polycarboxylates having a molecular weight of about 1,000 to about 5,000,000, preferably about 30,000 to about 500,000. Synthetic anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other anionic polycarboxylate polymers useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polyitaconic and polymaleic acids, and sulfonacrylic oligomers of M.W. as low as 1,000 available under the trade designation Uniroyal ND-2.

Also useful in the practice of the present invention are the so-called carboxyvinyl polymers, commercially available, for example, under the trade designation Carbopol 934, 940 and 941 from B. F. Goodrich, these polymers consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

The polycarboxylate polymer, when employed, is incorporated in the compositions of the present invention in weight amounts of about 0.05 to about 5%, preferably about 0.1 to about 3%.

Various other materials may be incorporated in the oral compositions of this invention including whitening agents such as urea peroxide, hydrogen peroxide, preservatives, such as sodium benzoate, vitamins and chlorophyll compounds and desensitizing agents such as potassium chloride and potassium nitrate. These adjuvants, when present, are incorporated in the compositions in amounts which do not substantially adversely affect the properties and characteristics desired.

The oral compositions of the present invention may be prepared by suitably mixing the ingredients. For instance, in the preparation of a mouthrinse, the 4-alkoxy substituted 2-hydroxybenzophenone antibacterial agent is dispersed in a mixture of ingredients, e.g. alcohol, humectants, anionic and betaine based surfactants and salts such as sodium fluoride and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The following Examples further illustrate the present invention, but it is understood that the invention is not limited thereto. All amounts and proportions referred to herein and in the appended claims are by weight unless otherwise indicated.

EXAMPLE

A dentifrice slurry was prepared using the following ingredients:

| Ingredients | Weight % |
| --- | --- |
| Glycerin (99.7% stock) | 20.0 |
| Sorbitol (70% stock) | 20.0 |
| Propylene glycol | 0.05 |
| Sodium lauryl sulfate | 1.0 |
| Betaine* | 1.0 |
| Sodium fluoride | 0.24 |
| Oxybenzone | 0.5 |

-continued

| Ingredients | Weight % |
| --- | --- |
| Flavor oil | 1.0 |
| Water Q.S. to 100 | |

*Cocoamidopropyl betaine

The antiplaque efficacy of the dentifrice formulation was evaluated using A. viscosus as the test bacteria.

The evaluation was performed using whole human saliva, which is applied to eight hydroxyapatite (HAP) disks to form a pellicle. After 45 minutes of pellicle formation, the media flow is started and the plaque-forming bacteria is pumped across the disks. Then the saliva, together with bacteria media composed of proteose peptone, trypticase peptone, potassium chloride, cysteine hydrochloride, yeast extract, and dextrose, is continuously pumped through the chamber at the rate of 1 ml/min. After four hours, a 10 mL treatment of dentifrice slurry is applied across the HAP disks, after which the saliva flow, at 1 ml/min., is resumed for 10 minutes to wash out residual slurry. After six hours the same procedure (involving a 30-second dentifrice slurry treatment) is repeated for a total of four treatments over three days. After 72 hours the resulting HAP disks are removed and added to two milliliters of 0.025% Trypsin solution and incubated for 45 minutes. The disks are then removed and the solution is sonicated for three seconds. The bacterial growth into the HAP disks is measured as turbidity or optical density of the Trypsin solution at an absorbance at 610 nm using a spectrophotometer. Optical density measurements indicate the degree of plaque growth on the plates, that is, the lower the optical density, the greater the antiplaque efficacy of the dentifrice slurry being tested.

For purposes of comparison the procedure of the Example was repeated except that 2% by weight betaine was substituted for the SLS/Betaine mixture (Dentifrice C) or 2% SLS was substituted for the SLS/betaine surfactant mixture (Dentifrice C1). The results of the evaluation are recorded in the Table below. A commercial dentifrice which contained 2% by weight SLS and no antibacterial agent was used as a control.

TABLE

| Dentifrice | Optical Density | Percent Reduction vs Control ($p < 0.05$) |
| --- | --- | --- |
| Control | 0.60 ± 0.05 | — |
| Example | 0.11 ± 0.01 | 62 |
| C | 0.18 ± 0.03 | 41 |
| C1 | 0.18 ± 0.04 | 40 |

The results recorded in the Table show that the dentifrice containing oxybenzone and the SLS/betaine surfactant combination exhibited significantly better antiplaque activity than the comparative dentifrices (C and C1) which contained only SLS or betaine.

What is claimed is:

1. An oral antiplaque composition which exhibits heightened antibacterial efficacy against plaque causing oral bacteria which is comprised of an orally acceptable vehicle containing a mixture of anionic and amphoteric betaine based surfactants and an effective antiplaque amount of a 4-alkoxy substituted 2-hydroxy benzophenone having the formula:

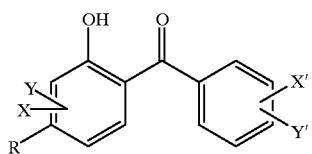

where X, Y, X' and Y' represent hydrogen, and lower straight chain or branched $C_1$–$C_4$ alkyl radicals, $C_3$–$C_6$ cycloalkyls and R represents lower $C_1$–$C_8$ alkoxy radical combinations thereof and salts thereof.

2. The composition of claim 1 wherein the 4-alkoxy substituted 2-hydroxy benzophenone is present in the oral composition in an amount in the range of about 0.003 to about 5.0% by weight.

3. The composition of claim 1 wherein the benzophenone compound is 2-hydroxy-4-methoxy benzophenone.

4. The composition according to claim 1 wherein the anionic surfactant is sodium lauryl sulfate.

5. The composition according to claim 1 wherein the amphoteric betaine based surfactant is an amido betaine.

6. The composition of claim 5 wherein the amidobentaine is cocoamidopropyl betaine.

7. The composition of claim 1 wherein the anionic and betaine based surfactants are present at a ratio of 1:1.

8. A method of promoting oral hygiene comprising applying to a dental surface an effective amount of a composition as defined in claim 1.

9. The method of claim 8 wherein the 4-alkoxy substituted 2-hydroxy benzophenone is present in the composition in an amount in the range of about 0.003 to about 5.0% by weight.

10. The method of claim 8 wherein the benzophenone compound is 2-hydroxy-4-methoxy benzophenone.

11. The method according to claim 8 wherein the anionic surfactant is sodium lauryl sulfate.

12. The method according to claim 1 wherein the amphoteric betaine based surfactant is an amidobetaine betaine.

13. The method according to claim 12 wherein the amidobetaine is cocoamidopropyl betaine.

14. The method according to claim 8 wherein the anionic and amphoteric betaine based surfactants are present at a ratio of 1:1.

* * * * *